(12) United States Patent
Kritzler

(10) Patent No.: US 9,179,669 B2
(45) Date of Patent: Nov. 10, 2015

(54) BIOSTATIC POLYMER FORMED ARTICLES

(75) Inventor: Steven Kritzler, Cronulla (AU)

(73) Assignee: Novapharm Research (Australia) PTY LTD, Rosebery (AU)

( * ) Notice: Subject to any disclaimer, the term of this patent is extended or adjusted under 35 U.S.C. 154(b) by 335 days.

(21) Appl. No.: 11/883,519

(22) PCT Filed: Feb. 2, 2006

(86) PCT No.: PCT/AU2006/000131
§ 371 (c)(1),
(2), (4) Date: Mar. 10, 2008

(87) PCT Pub. No.: WO2006/081618
PCT Pub. Date: Aug. 10, 2006

(65) Prior Publication Data
US 2008/0167383 A1    Jul. 10, 2008

(30) Foreign Application Priority Data

Feb. 2, 2005 (AU) ............................ 2005900444

(51) Int. Cl.
*A01N 33/12* (2006.01)
*C08K 5/00* (2006.01)
*C08K 5/19* (2006.01)
*C09D 129/04* (2006.01)

(52) U.S. Cl.
CPC .............. *A01N 33/12* (2013.01); *C08K 5/0058* (2013.01); *C08K 5/19* (2013.01); *C09D 129/04* (2013.01)

(58) Field of Classification Search
CPC ....... A01N 33/12; A01N 25/10; A01N 25/24; C08K 5/0058; C08K 5/19; C09D 129/04; C08L 29/04
USPC ................. 523/122; 424/76.1, 486, 424, 405, 424/78.08
See application file for complete search history.

(56) References Cited

U.S. PATENT DOCUMENTS

| | | | |
|---|---|---|---|
| 2,963,461 A * | 12/1960 | Pockel | 524/287 |
| 3,156,009 A * | 11/1964 | Alsys | 425/86 |
| 4,007,137 A * | 2/1977 | Sanders et al. | 512/24 |
| 4,469,837 A * | 9/1984 | Cattaneo | 524/388 |
| 4,692,494 A * | 9/1987 | Sonenstein | 525/57 |
| 4,885,105 A * | 12/1989 | Yang et al. | 510/296 |
| 5,137,969 A * | 8/1992 | Marten et al. | 525/56 |
| 5,421,898 A | 6/1995 | Cavanagh | |
| 6,270,754 B1 * | 8/2001 | Zhou et al. | 424/78.08 |
| 6,364,987 B1 * | 4/2002 | Takada et al. | 156/244.11 |
| 6,528,569 B1 * | 3/2003 | Oza et al. | 524/442 |
| 2002/0161088 A1 * | 10/2002 | Kochvar et al. | 524/379 |
| 2005/0129766 A1 * | 6/2005 | Bringley et al. | 424/486 |

FOREIGN PATENT DOCUMENTS

| | | |
|---|---|---|
| EP | 0 063 329 | 10/1982 |
| EP | 0 453 112 | 10/1991 |
| GB | 1124120 | 8/1968 |
| JP | 45-12227 | 4/1970 |
| JP | 61-180701 A | 8/1986 |
| JP | 63-068502 A | 3/1988 |
| JP | 05-163369 A | 6/1993 |
| JP | 10-249922 | 9/1998 |
| JP | 11-246309 | 9/1999 |
| NZ | 244898 | 11/1994 |
| WO | WO 00/18365 | 4/2000 |
| WO | WO 01/22948 A1 | 4/2001 |

OTHER PUBLICATIONS

Fred W. Billmeyer, Jr, "Textbook of Polymer Science, 3rd Edition" John Wiley & Sons, Inc., New York pp. 457-458 (1984).*
S.K. Saxena, Polyvinyl Alcohol (PVA) Chemical and technical Assessment (CTA)—FAO 2004 pp. 1-3, obtained online from http://www.fao.org/fileadmin/templates/agns/pdf/jecfa/cta/61/PVA.pdf.*

* cited by examiner

*Primary Examiner* — Alexander Kollias
(74) *Attorney, Agent, or Firm* — Wolf, Greenfield & Sacks, P.C.

(57) ABSTRACT

Compositions comprising a polyvinyl alcohol in combination with a biocide which is a plasticizer, such as a quaternary ammonium compound, or in combination with a biocide and a compatible plasticizer, and wherein the biocide forms a complex with the polyvinyl alcohol, said combination having been heated to above its melting point, said composition having a surface which remains biostatic or biocidal for at least 7 days. A hot melt of the composition may be cast or applied as a film or coating or may be extruded molded or otherwise into articles. Volatiles formed during heating may be removed from the combination e.g. by low pressure.

26 Claims, No Drawings

BIOSTATIC POLYMER FORMED ARTICLES

RELATED APPLICATIONS

This application is a national stage filing under 35 U.S.C. §371 of international application PCT/AU2006/000131, filed Feb. 2, 2006, which was published under PCT Article 21(2) in English.

FIELD OF THE INVENTION

This invention relates to a method and composition for making a film or formed article which has a biostatic or biocidal surface. Articles which are cast, extruded, moulded or otherwise formed according to the invention have a surface which resists microbial colony growth thereupon for a long period.

BACKGROUND OF THE INVENTION

Any discussion of the prior art throughout the specification should in no way be considered as an admission that such prior art is widely known or forms part of common general knowledge in the field.

It is well known that infection may be transmitted from one person to another by direct contact, by inhalation of air borne infectious particles, or by contact with infectious fluids. Infection is also commonly transmitted indirectly for example by contact with a surface that has itself become infected by contact with an infected person, or with infected airborne particles, or fluids.

For example hospital taps are a notorious for their potential to transmit infection and this has been to some extent alleviated by the use of elbow lever taps. But inside hospitals microbial agents such as bacteria, spores, viruses and fungi can also be indirectly transmitted by staff handling instruments, instrument sterilizing baths, door handles, and by touching many other surfaces. Both inside and outside of hospitals infections are spread via contact with toilet cubicle surfaces, toilet flushing buttons/levers, toilet doorhandles, telephone handsets, lift buttons, furniture and building surfaces, documents, and utensils to name but a few of countless examples. Surfaces of all of these typically harbour significant and rapidly growing colonies of microbes, moulds and the like. The invention also extends to include surfaces on which slimes and the like may harbour microbes such as tubing, surfaces in water treatment plants and the like and tubing.

The risk of infection from such like surfaces is reduced by regular cleaning with disinfectant solutions. However it is not practical to wipe such surfaces sufficiently often to provide effective disinfection.

No disinfectants for application to surfaces have been sufficiently durable to maintain a biostatic or biocidal surface for long periods in use. Attempts to incorporate disinfectants into solid articles for slow release have either not proven sufficiently durable, or have not been sufficiently effective or have been too toxic or expensive and none has been commercially successful.

It is an object of the present invention to overcome or ameliorate at least one of the disadvantages of the prior art, or to provide a useful alternative.

BRIEF DESCRIPTION OF INVENTION

According to one aspect the invention provides a composition comprising a polyvinyl alcohol in combination with a biocide which is a plasticizer, or in combination with a biocide and a compatible plasticiser, and wherein the biocide forms a complex with the polyvinyl alcohol, said combination having been heated to above its melting point, said composition having a surface which remains biostatic or biocidal for at least 7 days.

In a preferred embodiment the biocide is the plasticizer and no additional plasticisers are required. However, if desired additional plasticisers may be added. Alternatively a biocide may be selected in combination with a compatible plasticiser and in that case the biocide need not itself be a plasticiser provided that it forms a complex with the polyvinyl alcohol.

In highly preferred embodiments the biocide is a quaternary ammonium compound which acts as the sole plasticiser and the surface remains biostatic or biocidal for very much longer periods than 7 days. Preferred embodiments are free of microbes after manufacture, and prevent microbial colony growth on the surface after a period of months, even when the surface has been subjected to running water continuously in the interim.

It is believed that a complex formed by hydrogen bonding between the biocide and the polyvinyl alcohol prevents or inhibits leaching of biocide from the surface of the article.

Other embodiments of the invention provide a film or formed article manufactured from a polyvinyl alcohol incorporating a plasticizer, and a biocide which forms a complex with the polyvinyl alcohol. In a preferred such embodiment the biocide is a quaternary ammonium compound; and the plasticizer is a phenoxy ethanol, a suitable high boiling alcohol, ether, ester or the like. In preferred embodiments the surface remains biostatic or biocidal for very much longer periods than 7 days and it is believed will do so for the life of the article.

The present invention also provides composition in the form of a melt which comprise a polyvinyl alcohol in combination with a biocide which is a plasticizer, or in combination with a biocide and a compatible plasticiser, and wherein the biocide forms a complex with the polyvinyl alcohol. The melt may be hot and/or flowable, or cooled and/or solidified.

According to a second aspect the invention provides a method for forming an article having a biostatic or biocidal surface, comprising the steps of combining a polyvinyl alcohol with a biocide which is a plasticiser, or with a biocide and a plasticiser, and wherein the biocide forms a complex with the polyvinyl alcohol, and heating the combination to above its melting point.

Desirably any acid evolved during heating is removed by incorporation of an acid scavenger or is removed as volatiles for example by reduced pressure. Suitable acid scavengers are exemplified by metal hydroxides, for example magnesium hydroxide, or suitable amines An article may be formed from the resulting composition e.g. by extrusion of the melt.

For preference the biocide is a quaternary ammonium biocidal compound which itself acts as a plasticizer. A combination of plasticizers may be used and the combination may include those which are biocides or those which are not. For example, some quaternary compounds which are good biocides and which form complexes with polyvinyl alcohol are not good plasticisers and may be used as the biocide in combination with other more effective compatible plasticisers Preferably the materials are first blended and then the blend is extruded in an extrusion machine having at least one, and preferably a plurality of ports along the extrusion outlet channel from which volatiles may be removed under low pressure during the extrusion process. Desirably the blend is heated during extrusion to a temperature in the range of from 90° C. to 220° C., and more preferably from 140° C. to 210° C., and more preferably still at 190° C. to 200° C. The extrudate may be pelletized and used as a raw material for a casting, moulding (including injection and blow moulding) or other forming processes. In less preferred embodiments, it is envisaged that a suitable blend melt may be formed in a reactor under vacuum and then cast or extruded.

For preference the composition comprises from 20%-75% of polyvinyl alcohol and from 0.5%-25% of a quaternary ammonium biocide. However if the polyvinyl alcohol is combined with other polymers or copolymers, or fillers, the composition as a whole may contain down to 0.5% wt of polyvinyl alcohol. In preferred embodiments, the polyvinyl alcohol has a degree of polymerization such that its viscosity is from 25-30 cp in a 1% aqueous solution at 20° C. and has a degree of hydrolysis such that in excess of 97.5% of the acetate groups have been hydrolysed to hydroxyl groups. However for moulding more rigid articles, a polyvinyl alcohol having a significantly higher degree of polymerisation (and consequently viscosity in solution) is preferred Polyvinyl alcohol normally begins to decompose at around 140° C. which is below its melting point. Consequently prior attempts to extrude or mould polyvinyl alcohol by itself have merely resulted in the composition decomposing under the influence of heat and pressure. This has been overcome by the addition of polyalcohol plasticizers such as glycerine and pentaerythritol together with addition of metal hydroxides to the blend being extruded. The resulting polymers are expensive and with the exception of some low alcohol polyvinyl alcohol polymers which are readily soluble in water, they have no particular properties which have been considered useful commercially. None of the prior art polymers were biostatic or biocidal. In the present invention low pressure can be used to remove volatiles from the components during heating and this assists in avoiding decomposition and/or one or more acid scavengers may be added to avoid decomposition during heating.

The present inventors have found that under certain conditions polyvinyl alcohol can be formed into shapes and that when a quaternary ammonium compound is included, it forms a complex with the polyvinyl alcohol. Evidence for complex formation resides in a significant shift in the infra red spectrum of a the OH group peak from 3296 cm$^{-1}$ in pure polyvinyl alcohol to 3346 cm$^{-1}$ in mixtures with the quaternary ammonium biocide indicative of very significant levels of hydrogen bonding. The quaternary ammonium compound serves as a plasticizer but is also effective at the surface of the article to confer longstanding biostatic or biocidal properties.

The surface of the article is free of microbes when formed (i.e. is disinfected) and the formed article remains biostatic or biocidal for long periods. By biostatic is meant that microbial colonies (if any) on the surface do not grow or multiply. By biocidal is meant that bacteria (but not necessarily mycobacteria) and fungi on the surface are killed. By "long periods" in this context is meant a period of at least weeks, preferably months, and more preferably years. If the surface subsequently becomes contaminated it may be disinfected (e.g. by treatment with a disinfectant) and will thereafter again resist microbial colony growth for a long period.

Furthermore, the articles of the present invention present a fresh biostatic or biocidally active surface if the article is cut, scarred, scratched or otherwise disrupted. This is in contrast to coated articles, which, when the integrity of the coating is disrupted, can in some cases harbour bacteria. Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

In preferred embodiments of the invention the quaternary ammonium compound is n alkyl dimethyl benzyl ammonium chloride and is present in the range of from 0.5% to 75% w/w of the dried composition and more preferably 0.5% to 25%.

The present inventors have discovered that a combination of a polyvinyl alcohol with a quaternary ammonium biocide results, after melting under conditions which avoid decomposition, in a composition which is biostatic, that is to say on which micro organisms do not grow.

The extruded composition may be dissolved in a solvent and used to form a film with which to coat a surface, or may be used to cast a film, but preferably is extruded to form a sheet, tube, extruded moulding of indefinite length, or may be pelletized and the pellets may be recycled or used to mould or otherwise form an article by known techniques, the article having a surface which is biostatic and remains so for long periods.

The combination may optionally include adhesion promoters, vehicles, pigments and the like, and may include acid scavengers such as metal hydroxides or amines.

The term "polyvinyl alcohol" as herein used includes all resins made by the hydrolysis (saponification) of polyvinyl esters, for example polyvinyl acetate. The properties of the resins vary according to the degree of polymerization of the parent polyvinyl ester and the extent of the hydrolysis (saponification degree). In the case of a polyvinyl alcohol prepared from polyvinyl acetate the structure of polyvinyl alcohol may be represented by

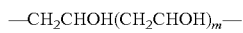

$$-CH_2CHOH(CH_2CHOH)_m-$$

where "1+m" is the degree of polymerization. On partial hydrolysis proportional amounts of residual CH$_2$COO— groups are distributed along the chain in place of OH and the amount of such acetate groups expressed as a percentage is the acetate content. Thus in polyvinyl alcohol of 70% acetate content, 30% of the acetate groups of the original polyvinyl acetate were hydrolysed to hydroxyl groups, and 70% remain as acetate groups. This may be referred to as 70% acetate content or as a 30% alcohol. In commercial grades "low acetate" or "high alcohol" grades covers up to about 15% acetate (i.e. from 100% down to about 85% alcohol), "medium acetate" covers from about 15% to about 45% acetate and "high acetate" or "low alcohol" grades over 45% acetate (below about 55% alcohol).

The term "polyvinyl alcohol" as used herein includes all suitable grades, degrees of saponification and degrees of polymerization.

Polyvinyl alcohols may also be made by hydrolysing polyvinyl esters other than acetates, and the same principles apply to the polyvinyl alcohols so formed which may also be used in the invention. Preferred embodiments of the invention utilize polyvinyl alcohol having an average degree of hydrolysis of greater than 96 mole % hydrolysis, since such compositions are more resistant to removal by cold or warm water.

Quaternary Ammonium Compounds for Use in the Invention

The invention has been exemplified by reference to n-alkyl dimethyl benzyl ammonium chloride (also known as benzalkonium chloride) as the highly preferred quaternary biocide. Alkyl benzyl quaternary biocidal compounds are preferred; however those skilled in the art will recognise that other quaternary ammonium antimicrobial compounds may be used in the present invention.

It is preferred that the quaternary ammonium antimicrobial compound is selected from the group having a general formula:

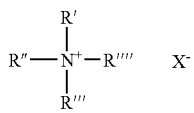

Wherein R' R" R'" R"" are alkyl radicals that may be the same or different, substituted or unsubstituted, branched or unbranched, and cyclic or acyclic. X is any anion but preferably a halogen, more preferable chlorine or bromine.

Highly preferred antimicrobial compounds are mono-long chain, tri-short chain, tetralkyl ammonium compounds, di-long-chain, di-short chain tetralkyl ammonium compounds and mixtures thereof where by "long".chain is meant about C6-C30 alkyl, and by "short" chain is meant C1-C5 alkyl, preferably C1-C3, or benzyl, or C1-C3 alkylbenzyl. Examples include monoallcyltrimethyl ammonium salts such as cetyltrimethyl ammonium bromide (CTAB), monoalkyldimethylbenzyl compounds or dialkylbenzyl compounds. Quaternary biocides such as chlorhexadine gluconate may be employed.

The most highly preferred compounds for use in the invention have at least one benzyl radical which may be a substituted benzyl. Examples include C8-C22 dimethyl benzyl ammonium chloride, C8-C22 dimethyl ethyl benzyl ammonium chloride and di-C6-C20 alkyl dimethyl ammonium chloride dimethyl benzyl ammonium chloride in a polymer compounder. The blend was then extruded and formed into moulded disks as described in Example 1

The quaternary ammonium compound is incorporated for broad spectrum (gram positive and gram negative) antibacterial properties.
Although the quaternary ammonium compound may comprise from 0.5% to 75% w/w of the dried film composition, it is preferred to employ more than 2% w/w of the dried film composition.

EXAMPLES OF THE INVENTION

Example 1

A composition consisting of 70 parts of polyvinyl alcohol having a degree of saponification of about 98.5% hydroxyl and a viscosity of 4.6-6.0 cps in a 1% solution at 20° C. was blended with 30 parts n-Alkyl (40% C12, 50% C14, 10% C16)dimethyl benzyl ammonium chloride in a polymer compounder. The blend was extruded in a D.S.M. brand laboratory scale mini extruder having a port on the extrusion barrel which was subjected to pressure reduction by a modestly sized vacuum pump. Commercial versions of this extruder have up to 10 ports on the extrusion barrel. The extrusion rate was 20 gm/min and the temperature was in the range 190° C. to 200° C. The extrudate was then used to feed an injection moulding apparatus which was used to produce disk shaped samples about 3 cm in diameter and 0.4 cm thick for testing.

Example 2

A composition consisting of 95 parts of polyvinyl alcohol having a degree of saponification of about 98.5% hydroxyl and a viscosity of 4.6-6.0 cps in a 1% solution at 20° C. was blended with 5 parts n-Alkyl (40% C12, 50% C14, 10% C16) quaternary ammonium chloride. Plasticizer selected from phenoxyethanol; 1-hexanol; 1-heptanol; 2-heptanol; 3-heptanol; 1-octanol; 2-octanol; 1-nonanol; octyleneglycol; 2-ethyl-1,3-hexanediol.

Example 3

A composition consisting of:
70 parts of polyvinyl alcohol having a degree of saponification of about 98.5% hydroxyl and a viscosity of 4.6-6.0 cps in a 1% solution at 20° C.;
17.5 parts of glycerine,
10 parts of pentaerythritol,
2 parts n-Alkyl (40% C12, 50% C14, 10% C16) dimethyl benzyl ammonium chloride, 0.5 parts of magnesium hydroxide
was blended in a polymer compounder. The blend was then extruded as in example 1 and sample disks prepared by injection moulding.

Example 4

Polyvinylalcohol; low molecular weight; % hydrolysis 96.5%-99.0% 70% w/w
Benzalkonium chloride 20% w/w
Plasticizer 10% w/w
Plasticizer selected from phenoxyethanol; 1-hexanol; 1-heptanol; 2-heptanol; 3-heptanol; 1-octanol; 2-octanol; 1-nonanol; octyleneglycol; 2-ethyl-1,3-hexanediol.

Example 5

Polyvinylalcohol; low molecular weight; % hydrolysis 96.5-99.0 96.0% w/w
Benzalkonium chloride 1.0% w/w
Plasticizer 3% w/w Moulded disks formed from composition according to examples 1-5 were tested for biostatic properties. The disks were inoculated with *Pseudomonas Originosa* ATCC 15442 (6.1 log concentration) in accordance with test method AOAC 955.17 and met the criteria for fungistatic efficacy.

Other disks were subjected to a stream of running water for 24 hours 7 days and 30 days and tested at the end of those periods. In each case the disks met the criteria of test method AOAC 955.17 for fungistatic efficacy. These tests are ongoing and the inventors are confident that the surfaces will maintain the bacteriostatic properties for the life of the article.

Biocidal properties of moulded disks made from a composition according to the examples were tested according to ASTM E2180-01 immediately after drying (t=0); after 7 days; and after 30 days with the following results:

| Time (t) | Result |
| --- | --- |
| 0 | Total kill |
| 7 days | Total kill |
| 30 days | Total kill |

While it is preferred to use a biocide which acts as both biocide and plasticizer, a combination of such biocide with other plasticizers may be used, or selected plasticisers may be employed with a biocide which is not itself a plasticizer but which forms a bond with the polyvinyl alcohol or plasticizer or both such as to inhibit leaching of the biocide from the article. Suitable plasticisers for use in the invention include phenoxyethanol; 1-hexanol; 1-heptanol; 2-heptanol; 3-heptanol; 1-octanol; 2-octanol; 1-nonanol; octyleneglycol; 2-ethyl-1,3-hexanediol; other high boiling point alcohols and polyols; and compatible ethers such as nonyl phenol condensed with two or three moles of ethylene oxide or esters of dibutyl phthalate or dioctyl phthalate such as used as PVC plasticizers.

It will be understood that compositions according to the invention may be combined with other suitable polymers or copolymers either by combining pellets of compositions according to the invention with the other polymers or by combining them prior to melting the Polyvinyl alcohol.

Compositions according to the invention may be coated as hot melts on and are effective on a wide range of surfaces including without limitation paper, textiles, plastics, metals, glass, and ceramics. The compositions may be extruded as sheets, rods, tubes or mouldings of indefinite length. Extruded compositions may be pelletised and recycled or the pellets may be used as raw material for moulding and forming processes to make articles of more complex shape. Compositions according to the invention may be incorporated into articles, (for example paper cups or food containers), or articles may be formed directly from the compositions when suitably formulated.

Those skilled in the art will be able to select combinations of polyvinyl alcohols and quaternary ammonium compounds for use in the invention based on the teaching hereof and to select appropriate ratios according to intended end product use. The invention extends to include the combination, solutions of the combination in appropriate solvents, and films or articles formed from the combination with or without solvents.

The claims defining the invention are as follows:

1. A composition in the form of a solidified melt, wherein the composition is formed by heating to a temperature in the range of from 140° C. to 220° C. in the absence of a solvent to form a melt and wherein the composition has a surface which remains biostatic or biocidal for at least 7 days, the composition comprising:
  from 20 to 96% by weight of the composition of a polyvinyl alcohol, wherein the structure of the polyvinyl alcohol is represented by the following structure:

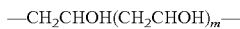
  —CH$_2$CHOH(CH$_2$CHOH)$_m$— where m is an integer greater than 0 and;
  from 0.5 to 75% by weight of the composition of a biocide given by the formula:

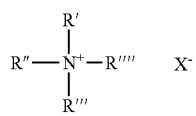

wherein R', R''', R'', and R'''' are alkyl radicals that are the same or different, substituted, aryl substituted alkyl unsubstituted, branched, unbranched, cyclic, or acyclic and X is an anion,
  wherein the biocide is a plasticizer, and
  wherein the biocide forms a complex with the polyvinyl alcohol.

2. The composition according to claim 1, wherein the biocide is an n-alkyl dimethyl benzyl ammonium chloride.

3. The composition according to claim 1, wherein the polyvinyl alcohol has a viscosity when measured in aqueous solution at 20° C. of greater than 4.6 cps.

4. The composition according to claim 1, wherein the composition includes an acid scavenger.

5. The composition of claim 1, wherein the polyvinyl alcohol is from 20 to 75% w/w of the composition.

6. A solution comprising the composition of claim 1 dissolved in a solvent.

7. An extruded sheet, tube, molding or pellet formed from the composition of claim 1.

8. An article impregnated or coated with the composition of claim 1.

9. A method of forming the composition of claim 1, the method comprising the steps of:
  combining the polyvinyl alcohol with the biocide; and
  heating the combination in the absence of solvent to a temperature in the range of from 140° C. to 220° C. to form a melt.

10. The method according to claim 9, wherein the combination of polymer and biocide is heated during extrusion in an extruder having at least one port on the extruder barrel from which volatiles can be extracted.

11. The method according to claim 9, wherein the combination is heated to a temperature in the range of from 140° C. to 210° C.

12. The method according to claim 9, wherein the combination is heated to a temperature in the range of from 190° C. to 200° C.

13. The method according to claim 9, wherein the biocide is n-alkyl dimethyl benzyl ammonium chloride.

14. The method according to claim 9, wherein the polyvinyl alcohol has a viscosity when measured in aqueous solution at 20° C. of greater than 4.6 cps.

15. The method of claim 9, wherein the polyvinyl alcohol is from 20 to 75% w/w of the composition.

16. The method according to claim 9, wherein volatiles formed during heating are removed from the combination.

17. The method according to claim 16, wherein volatiles are removed under low pressure during heating.

18. The method according to claim 9, wherein the composition further includes an acid scavenger.

19. The method according to claim 18, wherein the acid scavenger is a metal hydroxide or an amine.

20. The method according to claim 9 further comprising the step of: casting, forming a film or a coating from a hot melt of the combination.

21. A method comprising the step of: impregnating or coating a substrate with the hot melt according to claim 20.

22. The method according to claim 9 further comprising the step of: extruding the composition as a sheet, tube or molding.

23. The method according to claim 22 further comprising the step: of forming a pellet from the extruded composition.

24. The method according to claim 23 further comprising the step of: molding or forming an article from the pellets.

25. A method comprising: the step of dissolving in a solvent a melted composition according to the composition claim 1.

26. A method comprising the step of: impregnating or coating a substrate with a solution according to claim 25.

* * * * *